(12) United States Patent
Chen et al.

(10) Patent No.: US 6,800,782 B2
(45) Date of Patent: Oct. 5, 2004

(54) ANHYDROUS CRYSTALLINE FORMS OF GABAPENTIN

(75) Inventors: Linna R Chen, West Linn, OR (US); Suresh R Babu, Canton, MI (US); Claude Jeffrey Calvitt, Saline, MI (US); Brian Tobias, Ann Arbor, MI (US)

(73) Assignee: Warner-Lambert Co., Morris Plains, NJ (US)

(*) Notice: Subject to any disclaimer, the term of this patent is extended or adjusted under 35 U.S.C. 154(b) by 118 days.

(21) Appl. No.: 10/256,155

(22) Filed: Sep. 25, 2002

(65) Prior Publication Data

US 2003/0092933 A1 May 15, 2003

Related U.S. Application Data

(60) Provisional application No. 60/328,375, filed on Oct. 9, 2001.

(51) Int. Cl.$^7$ ................................................ C07C 10/14
(52) U.S. Cl. ........................................................ 562/504
(58) Field of Search ................................. 562/504, 507

(56) References Cited

U.S. PATENT DOCUMENTS

| | | |
|---|---|---|
| 4,024,175 A | 5/1977 | Satzinger et al. |
| 4,087,544 A | 5/1978 | Satzinger et al. |
| 4,894,476 A | 1/1990 | Butler et al. |
| 4,960,931 A | 10/1990 | Butler et al. |
| 5,068,413 A | 11/1991 | Steiner et al. |

FOREIGN PATENT DOCUMENTS

| | | |
|---|---|---|
| EP | 1083164 | 3/2001 |
| WO | WO 98/28255 | 7/1998 |

Primary Examiner—Paul J. Killos

(57) ABSTRACT

Described are new crystalline anhydrous forms of gabapentin formed from gabapentin monohydrate. The new crystalline forms provide advantages in the manufacture of the therapeutic agent.

18 Claims, 5 Drawing Sheets

ANHYDROUS CRYSTALLINE FORMS OF GABAPENTIN

CROSS-REFERENCE TO RELATED APPLICATION

This application claims benefit of application Ser. No. 60/328,375 of Oct. 9, 2001, which application is incorporated herein by reference.

FIELD OF THE INVENTION

The present invention relates to new anhydrous crystalline forms of gabapentin prepared from gabapentin monohydrate.

BACKGROUND OF THE INVENTION

Gabapentin is a generic name used to identify the chemical compound (1-aminomethyl)-1-cyclohexaneacetic acid

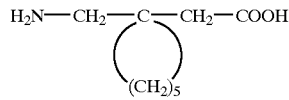

It is useful in therapy of certain cerebral disorders such as certain forms of epilepsy, faintness attacks, hypokinesia, and cranial traumas. U.S. Pat. Nos. 4,024,175 and 4,087,544 cover the compound and its uses. They also disclose an acid salt, i.e., gabapentin hydrochloride hydrate in a ratio of 4:4:1 and a sodium salt of gabapentin hydrate at a ratio of 2:1. U.S. Pat. No. 4,894,476 describes gabapentin monohydrate and a process for producing it. These patents are incorporated by reference.

SUMMARY OF THE INVENTION

The present invention provides new crystalline forms of gabapentin, dehydrate Form A and dehydrate Form B. These new crystalline forms are prepared from gabapentin monohydrate. The gabapentin monohydrate is dehydrated in an environment in which the water activity is maintained below about 0.8 to about 0.9, or heated at a temperature from about 50–175° C. to form the crystalline gabapentin dehydrate Form A. This crystalline form is then converted on standing at ambient temperatures to a more stable crystalline form of gabapentin, dehydrate Form B.

The present invention provides further process improvements to provide pure crystalline forms of the therapeutic agent, gabapentin. The present process eliminates the need of using organic solvents such as methanol described earlier in methods of producing gabapentin and its monohydrate. The present process offers faster manufacturing processing, better safety, less solvent disposal and less loss of yield upon recrystallization.

DETAILED DESCRIPTION OF THE PREFERRED EMBODIMENT

Figure 1:
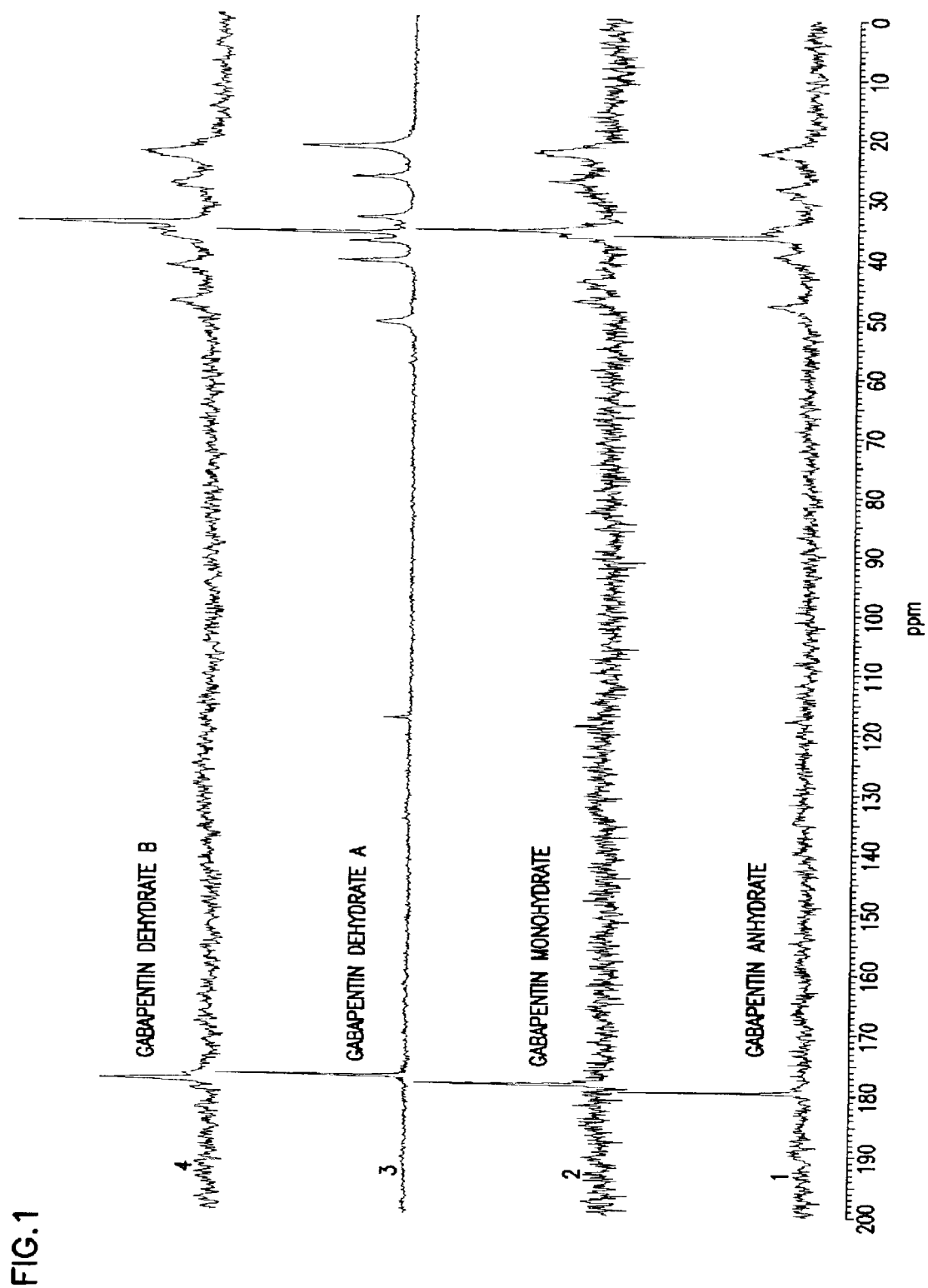
FIG. 1 shows the 13C-ssNMR spectra for the four crystalline forms of gabapentin.
Figure 2:
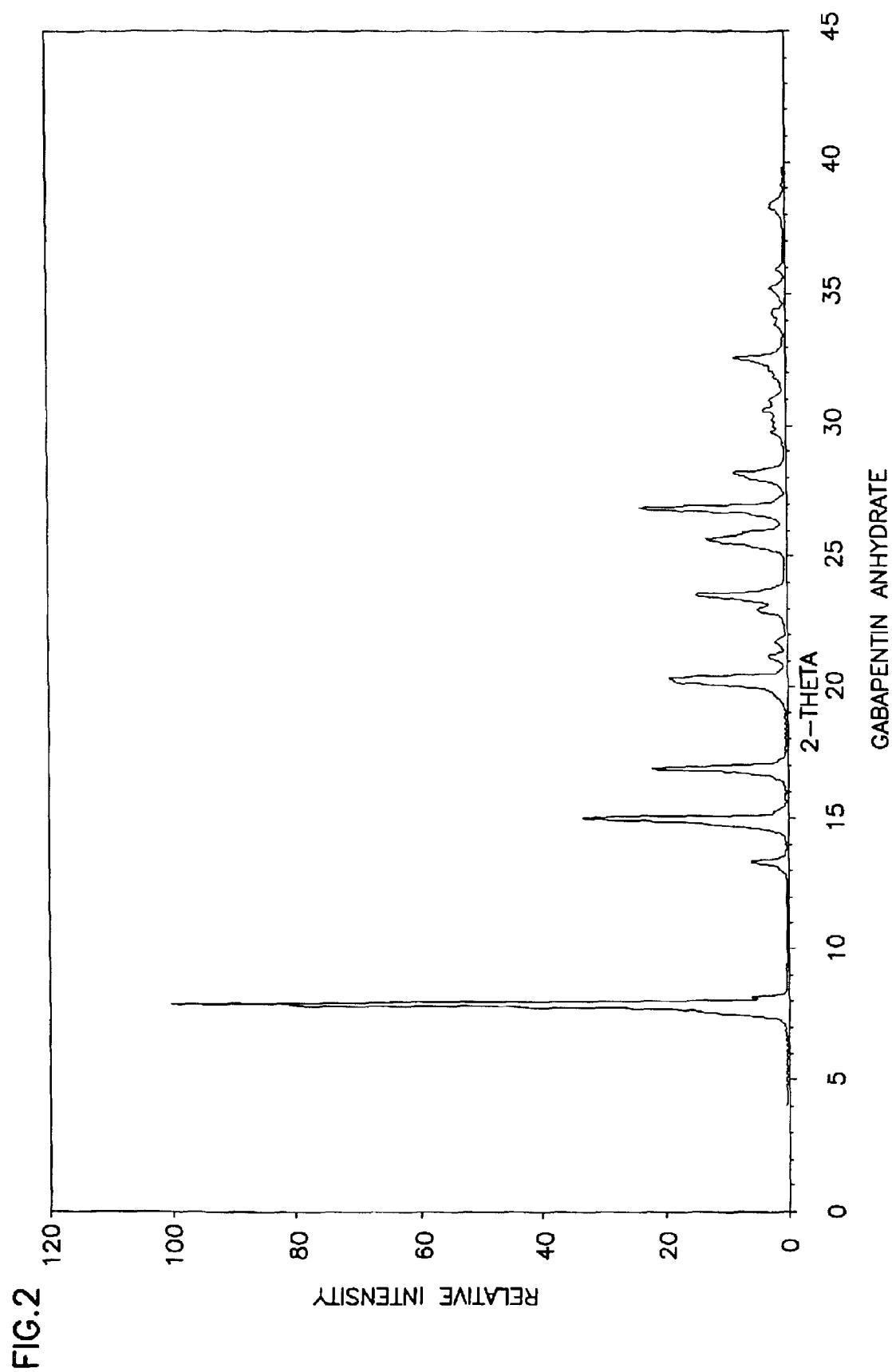
FIG. 2 shows the X-ray powder diffractogram for crystalline gabapentin anhydrate.
Figure 3:
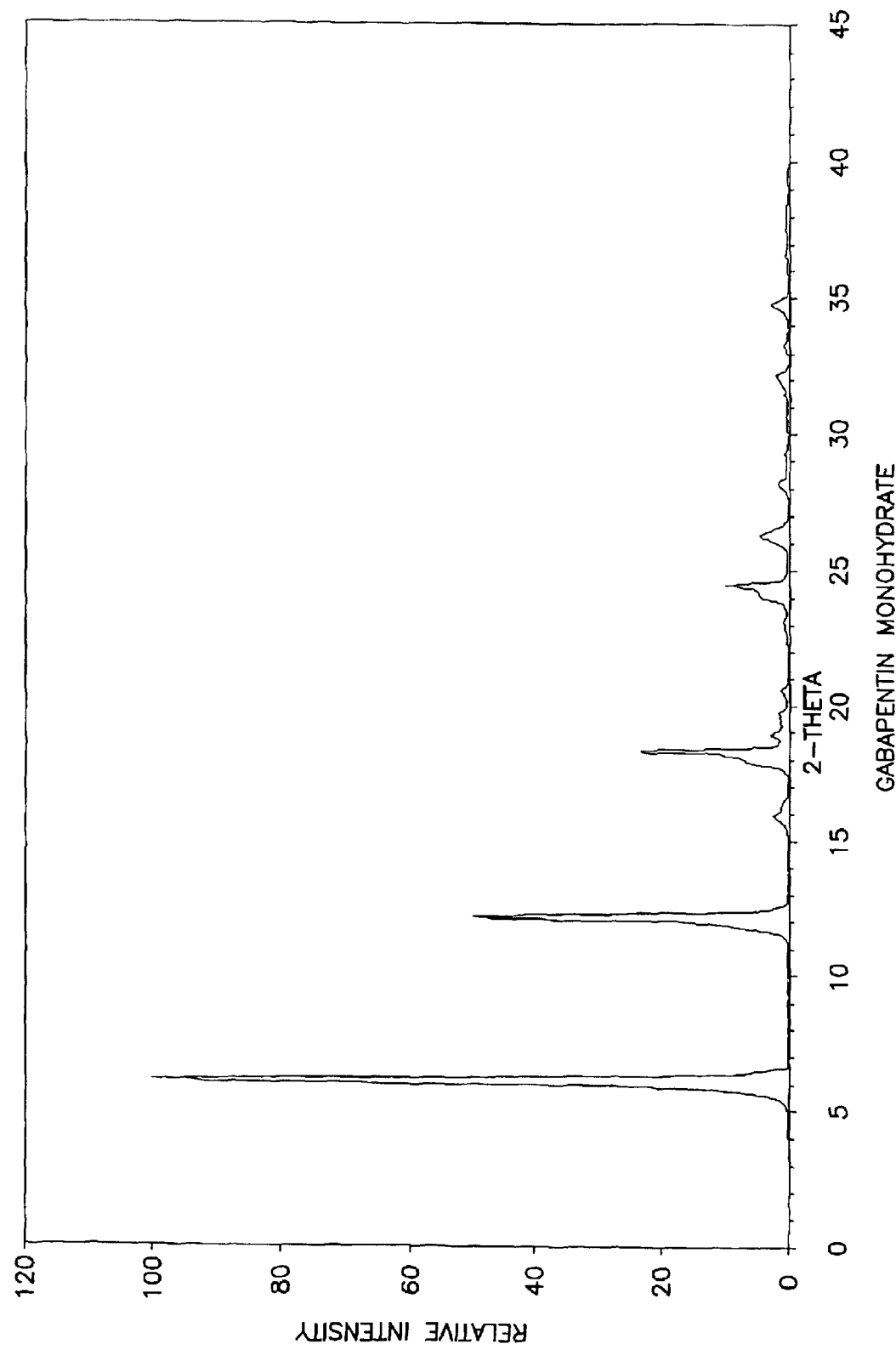
FIG. 3 shows the X-ray powder diffractogram for crystalline gabapentin monohydrate.
Figure 4:
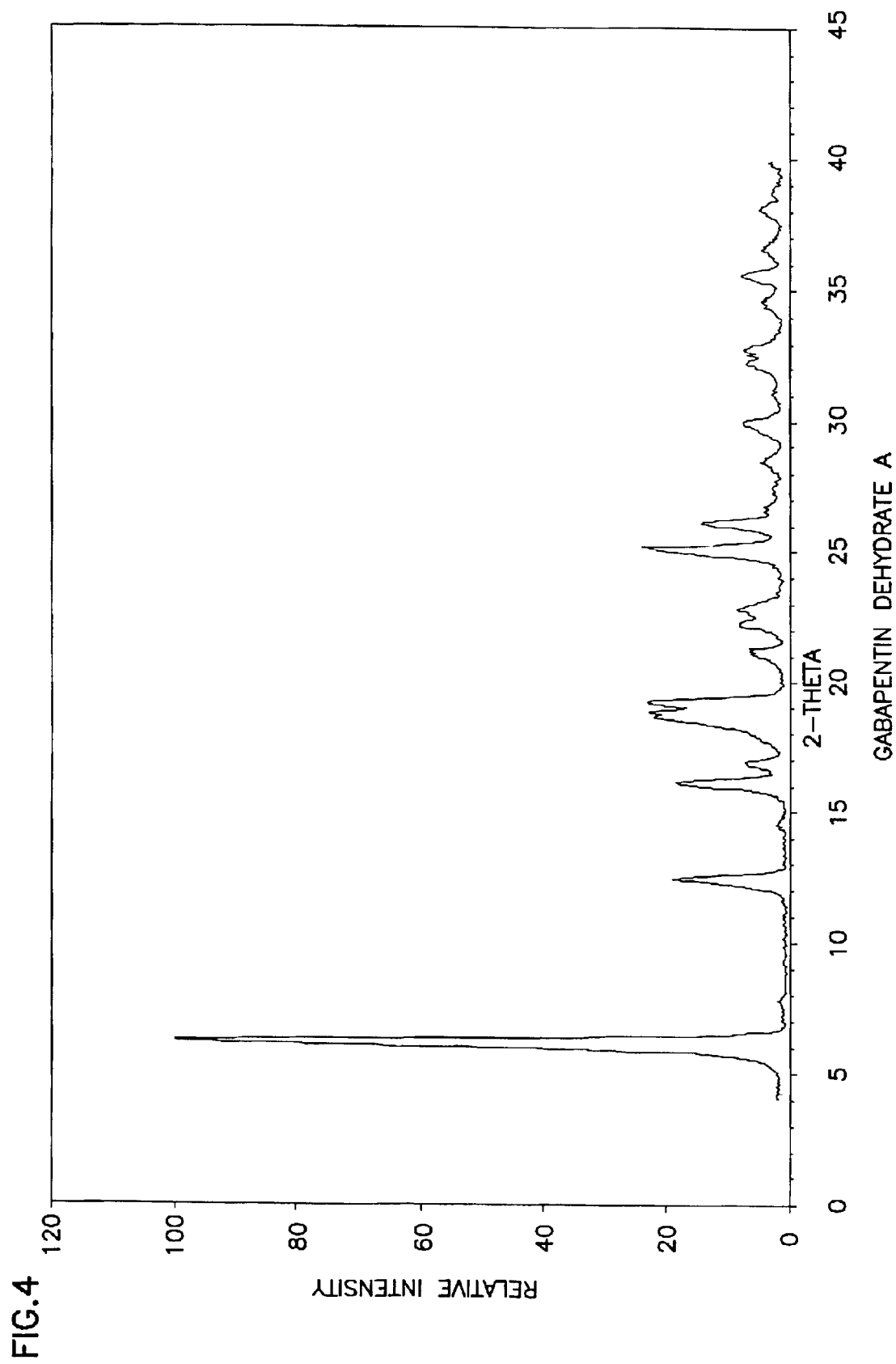
FIG. 4 shows the X-ray powder diffractogram for crystalline gabapentin dehydrate A.
Figure 5:
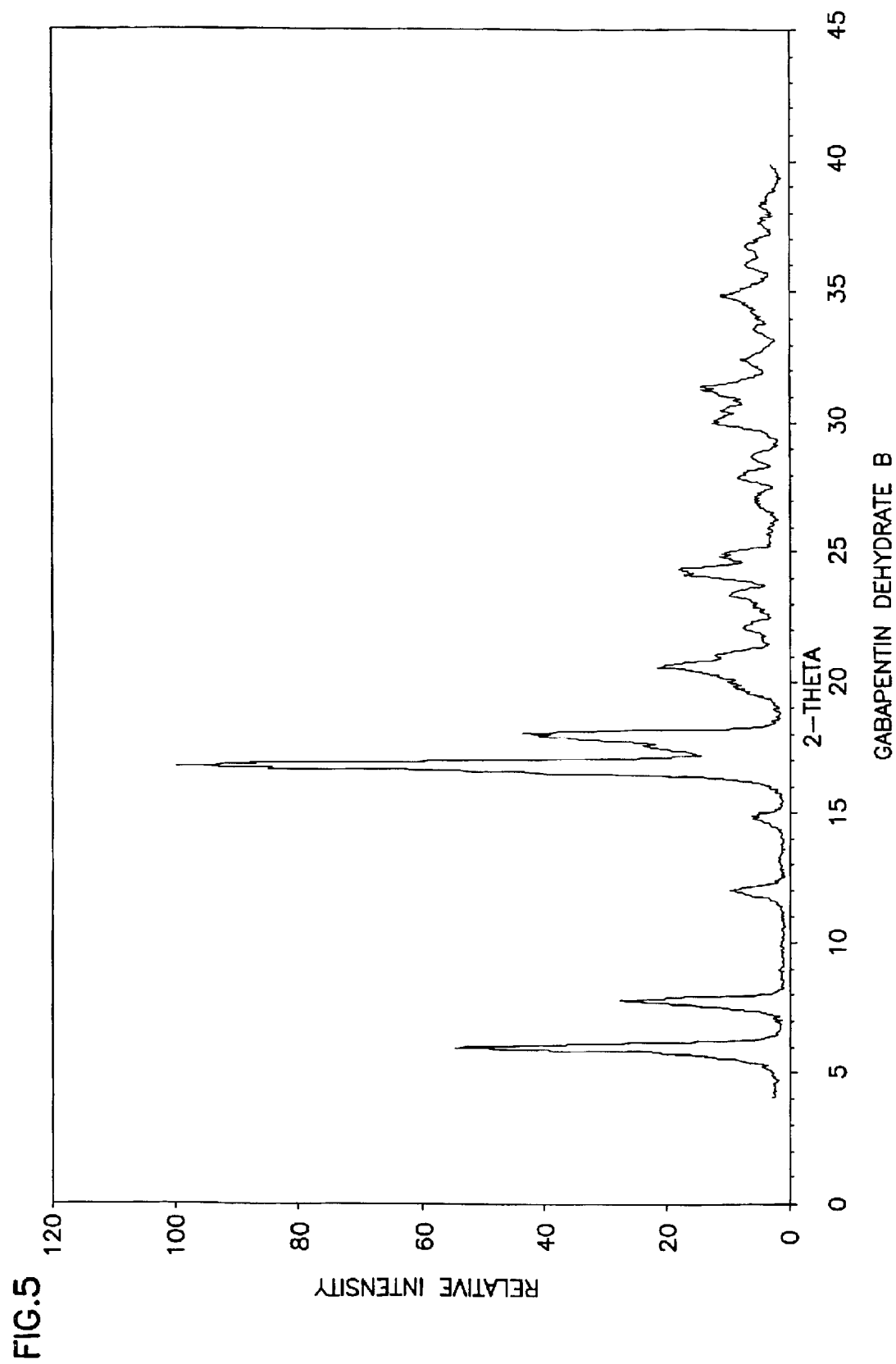
FIG. 5 shows the X-ray powder diffractogram for crystalline gabapentin dehydrate B.

The present invention provides novel crystalline forms of gabapentin, the dehydrate Form A and dehydrate Form B. The present invention also includes improvements in the preparation of gabapentin monohydrate, the precursor to the new crystalline dehydrate of the present invention. Initially, gabapentin monohydrate was reported in U.S. Pat. No. 4,894,476 as a new crystalline form for therapeutic purposes and also as a means of purifying commercial gabapentin, an anhydrous form, by reconversion of the monohydrate to gabapentin.

The present invention is based on a discovery that the known anhydrous form of gabapentin can only be crystallized from solvents or solvent mixtures with a water activity of less than about 0.8 to about 0.9 and gabapentin monohydrate can only be crystallized from water or solvent mixtures with a water activity of greater than about 0.8 to about 0.9. Gabapentin monohydrate can be prepared by suspending gabapentin in a solvent or solvent mixture having a water activity of at least about 0.8 to about 0.9, crystallizing the resulting monohydrate and collecting the product on a suction filter. Solvent mixtures include solvents that are miscible with water such as alcohol, preferably a lower alkanol such as methanol or ethanol.

Gabapentin dehydrate A can be produced from the monohydrate when the immediate environment surrounding the monohydrate has a water activity of less than approximately 0.85; i.e. less than between about 0.8 to about 0.9. (In the vapor phase this means that the relative humidity is less than 85%). This can be achieved by applying a vacuum, a desiccant, and/or applying heat.

For example, dehydrate A can be produced from the monohydrate at subambient temperatures provided the relative humidity is less than about 85% (water activity less than 0.85).

Typically, once the monohydrate is formed, drying the monohydrate at a temperature of about 50–175° C. or below the melting point of gabapentin will form dehydrate Form A. The heating process may take place until a constant weight of dehydrate Form A is obtained. Typically, heating may be carried out between about 70 and 100° C. and, for example, at about 80° C. for about three hours.

Gabapentin dehydrate Form A has been found to convert to a more stable crystalline form, dehydrate Form B on standing at ambient temperatures. The material may be allowed to stand, for example in an inert atmosphere or in a sealed container. The rate of conversion from dehydrate A to B is directly related to the purity of starting gabapentin dehydrate A.

Water content of the reported forms is less than 0.5% by weight whereas gabapentin monohydrate contains about 9% water by weight.

The novel crystalline forms have been characterized by their unique X-ray powder diffraction patterns and their characteristic chemical shifts in their respective solid state 13C NMR spectra.

Tables 1–4 below compare the two novel crystalline forms of gabapentin, dehydrate A and dehydrate B, to the known anhydrous crystalline form of gabapentin, and gabapentin monohydrate.

TABLE 1

Gabapentin PXRD Data

| 2-Theta | d(Å) | Intensity |
|---|---|---|
| 7.9 | 11.1 | 100 |
| 15.0 | 5.9 | 33 |
| 16.9 | 5.2 | 22 |
| 20.4 | 4.4 | 18 |
| 23.6 | 3.8 | 15 |
| 25.7 | 3.5 | 13 |
| 27.0 | 3.3 | 23 |

TABLE 2

Gabapentin Monohydrate PXRD Data

| 2-Theta | d(Å) | Intensity |
|---|---|---|
| 6.1 | 14.5 | 100 |
| 12.2 | 7.3 | 50 |
| 18.3 | 4.8 | 23 |
| 24.4 | 3.6 | 10 |

TABLE 3

Gabapentin Dehydrate A PXRD Data

| 2-Theta | d(Å) | Intensity |
|---|---|---|
| 6.2 | 14.2 | 100 |
| 12.5 | 7.1 | 18 |
| 16.1 | 5.5 | 18 |
| 18.8 | 4.7 | 21 |
| 19.2 | 4.6 | 22 |
| 25.1 | 3.5 | 21 |
| 26.1 | 3.4 | 11 |

TABLE 4

Gabapentin Dehydrate B PXRD Data

| 2-Theta | d(Å) | Intensity |
|---|---|---|
| 6.0 | 14.8 | 53 |
| 7.7 | 11.4 | 27 |
| 16.8 | 5.3 | 100 |
| 18.0 | 4.9 | 40 |
| 20.6 | 4.3 | 17 |
| 24.3 | 3.65 | 13 |

X-Ray (PXRD) data were acquired with a Rigaku Ultima+ X-Ray Powder Diffractometer equipped with a copper target operating at 40 kV/40 mA producing X-rays of wavelength 1.542 Angstroms. The divergence slit and scatter slit were both set at 1°. The receiving slit was set at 0.3 mm. The diffractometer was equipped with a Rigaku ASC-6A sample changer. Specimen preparation consisted of pouring a quantity of the sample sufficient to fill a sample plate and gently scraping the surface smooth and flat without packing the sample. Under ambient conditions, samples were scanned continuously from 4° to 40° 2-theta at a rate of 5°/minute. PXRD data for the four Forms are presented in Tables 1 through 4 above. The numbers are for peaks of at least 10% the intensity of the most intense peak and have been rounded off from the raw data representing an accuracy of about ±0.2 with regards to the 2-theta and d(Å) values given routine experimental error. PXRD diffractograms for the four Forms are shown in FIGS. 2–5.

Tables 5–8 compare the chemical shifts in parts per million (ppm) for the various crystalline forms of gabapentin including the novel crystalline forms of the present invention, dehydrate Form A and dehydrate Form B.

TABLE 5

Chemical Shifts(ppm) of Gabapentin 22.4
28.2
29.8
34.8
35.5
36.3
39.6
40.1
47.7
179.6

TABLE 6

Chemical Shifts(ppm) of Gabapentin Monohydrate 22.7
27.4
35.7
36.4
44.1
47.3
178.5

TABLE 7

Chemical Shifts(ppm) of Gabapentin Dehydrate A 22.1
27.0
33.7
36.2
37.6
41.0
51.0
177.4

TABLE 8

Chemical Shifts(ppm) of Gabapentin Dehydrate B 23.3
28.5
35.0
36.2
37.1
42.3
48.2
178.3

All 13C-ssNMR spectra were acquired with a Varian 400 MHz NMR spectrometer utilizing high power proton decoupling and cross-polarization with magic angle spinning at approximately 6 kHz. Chemical shifts were referenced to external hexamethylbenzene (methyl signal at 17.3 ppm). Each specimen was prepared by packing a sample into a 7 mm canister-design silicon nitride rotor using a packing tool and sealing the rotor with a cap. Spectra were acquired under ambient conditions. 13C-ssNMR spectra for the four Forms are shown in FIG. 1.

EXAMPLE

Example 1-Preparation of Gabapentin Monohydrate

Gabapentin anhydrate, 100 grams, was suspended in 480 mL of water and stirred for one hour with seeds of crystalline monohydrate added. Following crystallization, the gabapentin monohydrate was isolated by suction filtration.

Example 2-Crystalline Gabapentin Dehydrate Form A and B

Form A: Two batches of gabapentin monohydrate, 200 mg and 100 grams were heated at from 70–80° C. for three hours to provide gabapentin dehydrate Form A.

Density of the new dehydrate, Form A, was determined to be 1.156 grams/mL by hexane displacement method. Samples of the gabapentin dehydrate Form A were analyzed by Karl Fischer for water and by HPLC for gabapentin.

The dehydrate crystalline Forms A and B meet the water specification ($\leq 0.5\%$w/w) and the assay specification (98.5%–101.5%w/w on an anhydrous basis).

Elemental analysis and 1H NMR confirmed the chemical composition of gabapentin dehydrate Form A.

Vapor sorption analysis showed that gabapentin dehydrate Form A does not pick up significant amount of moisture (<0.5%) at 25° C. at relative humidity <85%.

Form B: The two batches of dehydrate Form A obtained above were allowed to stand. Within one month, Form A was found to convert to gabapentin dehydrate Form B by 20%. Within one year, complete conversion to dehydrate Form B was found. Samples of the batches were monitored by 13C-ssNMR until conversion was complete as evidenced by the disappearance of dehydrate Form A.

Both crystalline forms were characterized by their respective solid state NMR spectra and X-ray powder diffractograms.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A process for the preparation of crystalline gabapentin dehydrate Form B comprising:
   (a) dehydrating gabapentin monohydrate to form crystalline gabapentin dehydrate Form A, and
   (b) allowing dehydrate A to stand at ambient temperatures to form crystalline gabapentin dehydrate Form B.

2. The process of claim 1, where the dehydrating step (a) is carried out by applying a vacuum, a desiccant or heat.

3. The process of claim 1, wherein the gabapentin monohydrate is dehydrated in an environment in which water activity is maintained below about 0.8 and about 0.9.

4. The process of claim 1, wherein the dehydrating step (a) is in an environment with a relative humidity of less than about 85%.

5. The process of claim 2, wherein gabapentin monohydrate is heated to a constant weight of crystalline gabapentin dehydrate Form A.

6. The process of claim 2, wherein heat is applied at a temperature between about 50 to about 175° C.

7. The process of claim 6, wherein the temperature is between about 70 and about 100° C.

8. The process of claim 1, wherein dehydrate Form A is allowed to stand in an inert atmosphere or sealed container.

9. The process of claim 1, wherein gabapentin monohydrate is prepared from the following steps which comprise:
   (a) suspending gabapentin in a solvent or solvent mixture having a water activity value of greater than about 0.8 to about 0.9;
   (b) crystallizing and collecting gabapentin monohydrate on a filter.

10. The process of claim 9, wherein the solvent is water.

11. A crystalline gabapentin dehydrate Form A having an X-ray powder diffraction containing at least one of the following 2-theta values measured using $CuK_\alpha$ radiation: 18.8 or 25.1.

12. A crystalline gabapentin dehydrate Form A having an X-ray powder diffraction containing the following 2-theta values measured using $CuK_\alpha$ radiation: 18.8, 25.1 and 26.1.

13. A crystalline gabapentin dehydrate Form A having an X-ray powder diffraction containing the following 2-theta values measured using $CuK_\alpha$ radiation: 6.2, 12.5, 16.1, 18.8, 19.2, 25.1 and 26.1.

14. A crystalline gabapentin dehydrate Form A characterized by solid state 13C nuclear magnetic resonance having the following chemical shifts expressed in parts per million referenced to an external methyl signal at 17.3 ppm for hexamethylbenzene: 22.1, 27.0, 33.7, 36.2, 37.6, 41.0, 51.0 and 177.4.

15. A crystalline gabapentin dehydrate Form B having an X-ray powder diffraction containing at least one of the following 2-theta values measured using $CuK_\alpha$ radiation: 6.0 or 16.8.

16. A crystalline gabapentin dehydrate Form B having an X-ray powder diffraction containing the following 2-theta values measured using $CuK_\alpha$ radiation: 6.0, 16.8 and 18.0.

17. A crystalline gabapentin dehydrate Form B having an X-ray powder diffraction containing the following 2-theta values measured using $CuK_\alpha$ radiation: 6.0, 7.7, 16.8, 18.0, 20.6 and 24.3.

18. A crystalline gabapentin dehydrate Form B characterized by solid state 13C nuclear magnetic resonance having the following chemical shifts expressed in parts per million referenced to an external methyl signal at 17.3 ppm for hexamethylbenzene: 23.3, 28.5, 35.0, 36.2, 37.1, 42.3, 48.2 and 178.3.

* * * * *